United States Patent [19]

Maxwell et al.

[11] 4,214,472
[45] Jul. 29, 1980

[54] EXHAUST GAS OXYGEN SENSOR AND ELECTRICAL CONNECTOR ARRANGEMENT

[75] Inventors: Mary E. Maxwell, Livonia, Mich.; Ronald F. Froats, Windsor, Canada

[73] Assignee: Ford Motor Company, Dearborn, Mich.

[21] Appl. No.: 5,424

[22] Filed: Jan. 22, 1979

[51] Int. Cl.² ............................................. G01N 27/04
[52] U.S. Cl. ......................................... 73/23; 338/34; 339/60 R
[58] Field of Search .................. 73/23, 27 R; 338/34; 422/98; 204/195 S; 339/60 R, 91 R

[56] References Cited

U.S. PATENT DOCUMENTS

| 3,937,545 | 2/1976 | Cairns et al. ....................... 339/60 R |
| 4,001,758 | 1/1977 | Esper et al. .............................. 338/34 |

*Primary Examiner*—Stephen A. Kreitman
*Attorney, Agent, or Firm*—Robert W. Brown; Clifford L. Sadler

[57] ABSTRACT

An exhaust gas oxygen sensor and electrical connector arrangement for use in connecting the sensor to an electronic device capable of utilizing an electrical signal produced by the sensor. The electrical connector arrangement eliminates both male and female electrical connectors required in prior sensor electrical connector arrangements. The new electrical connector arrangement provides a leak-proof connection between a cylindrically-shaped sensor member and a connector assembly including an elastomeric grommet, a plastic sleeve and a plastic spacer used to retain connector terminals within the sleeve for receipt of cooperating terminals on the exhaust gas sensor. The connector-assembly sleeve and the cylindrically-shaped member of the oxygen sensor cooperate to produce a positive latching action of the connector assembly to the exhaust gas sensor.

8 Claims, 17 Drawing Figures

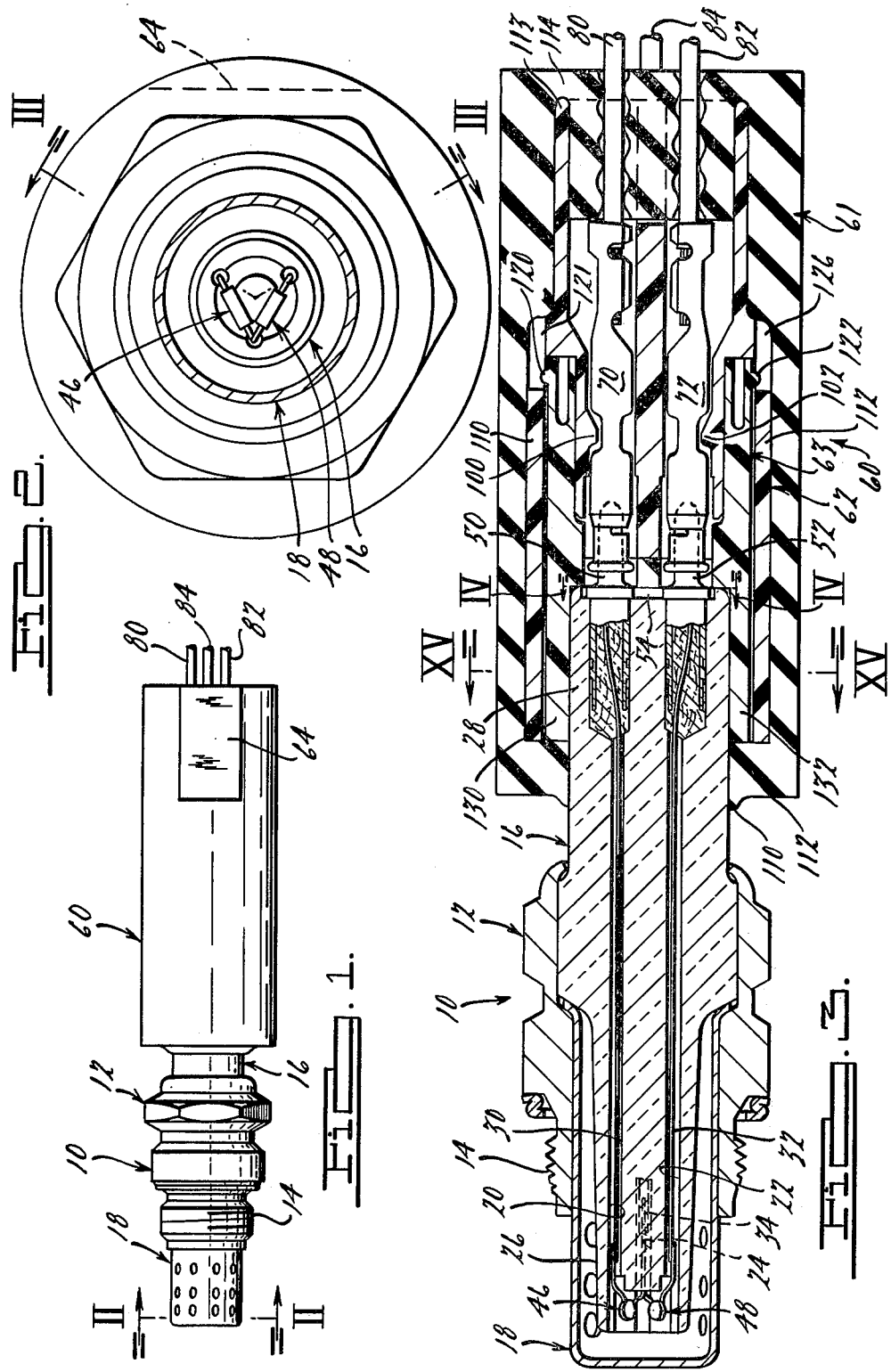

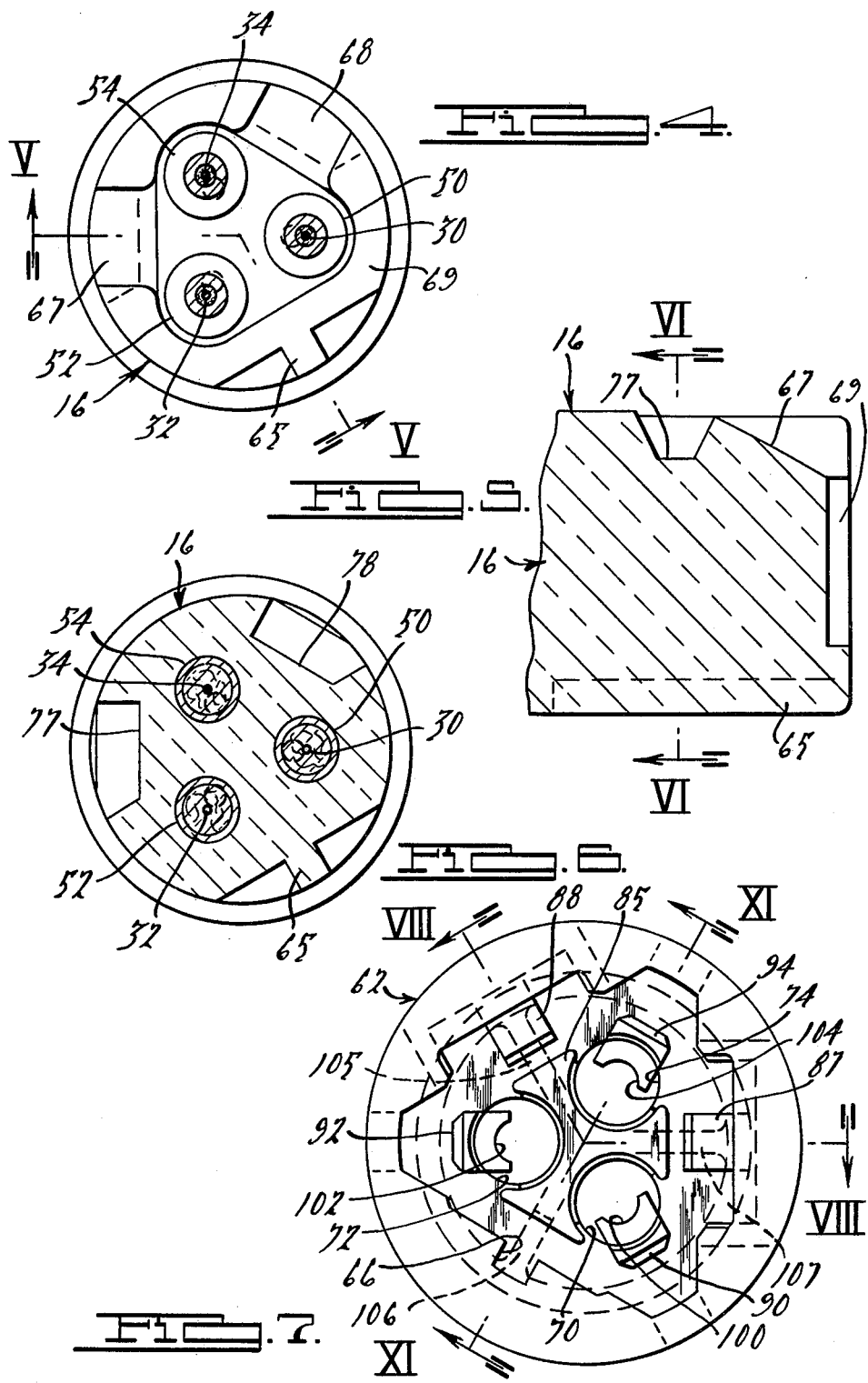

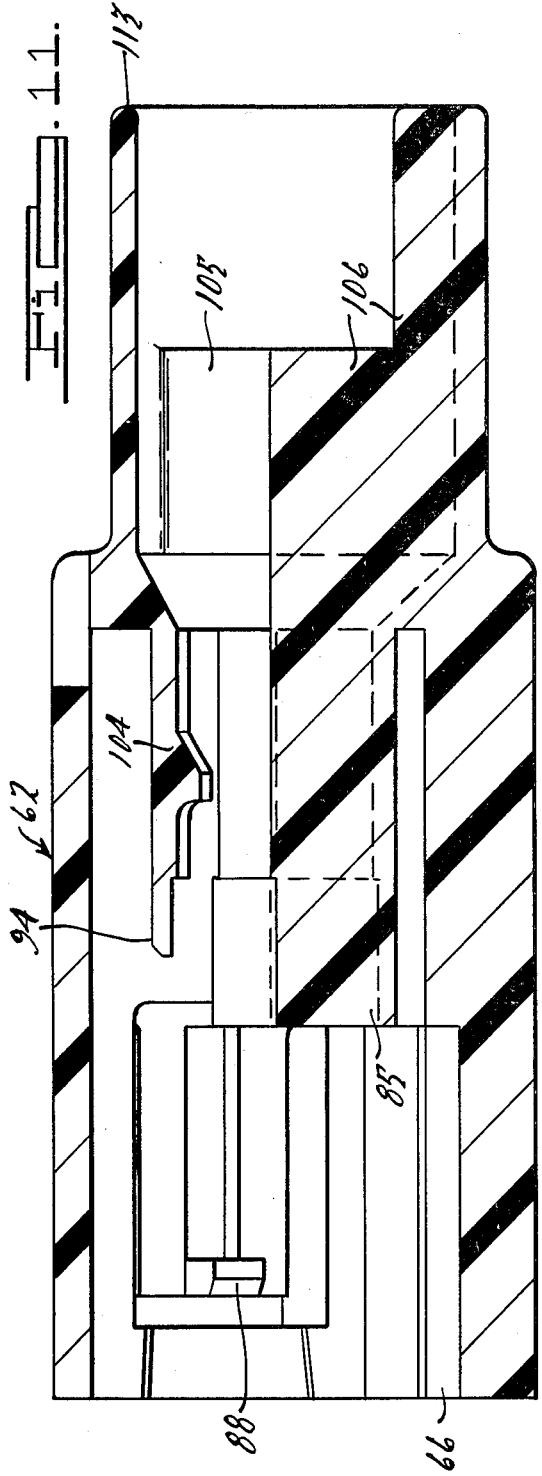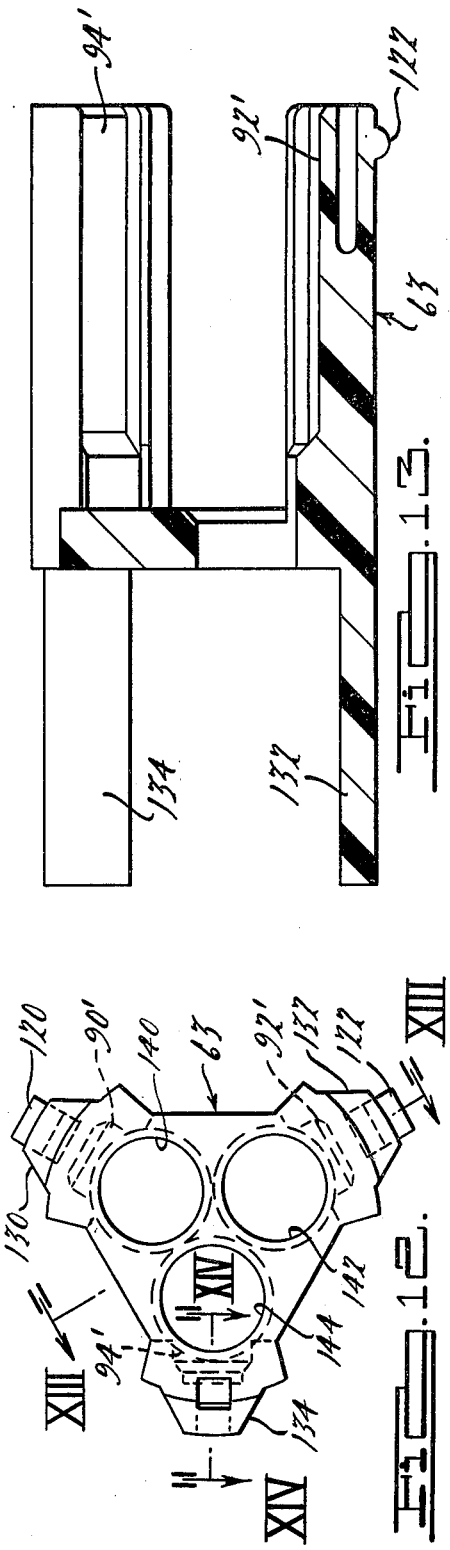

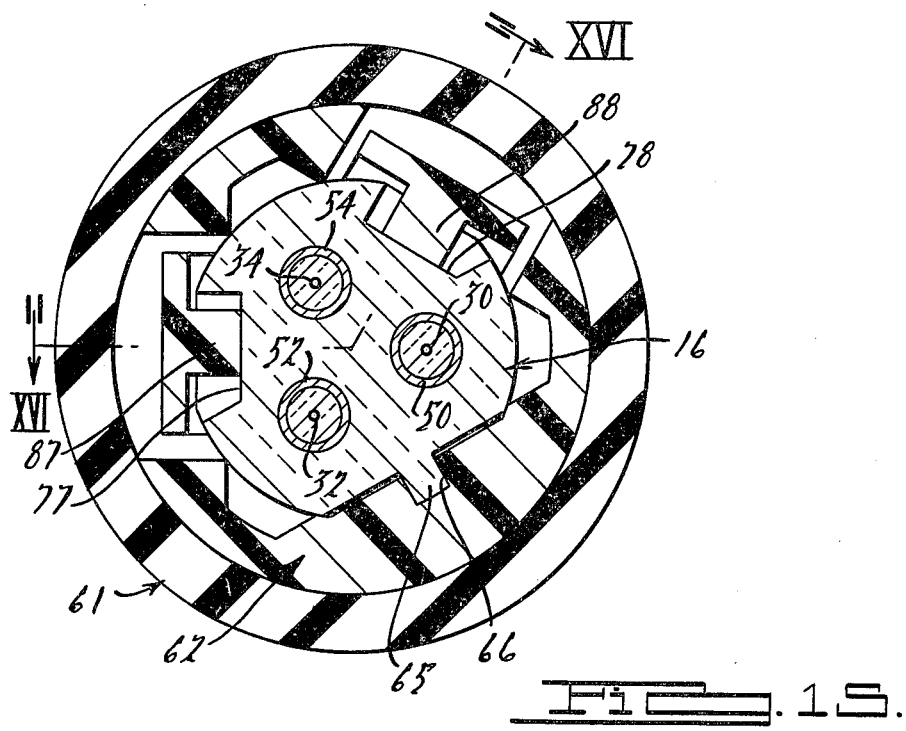
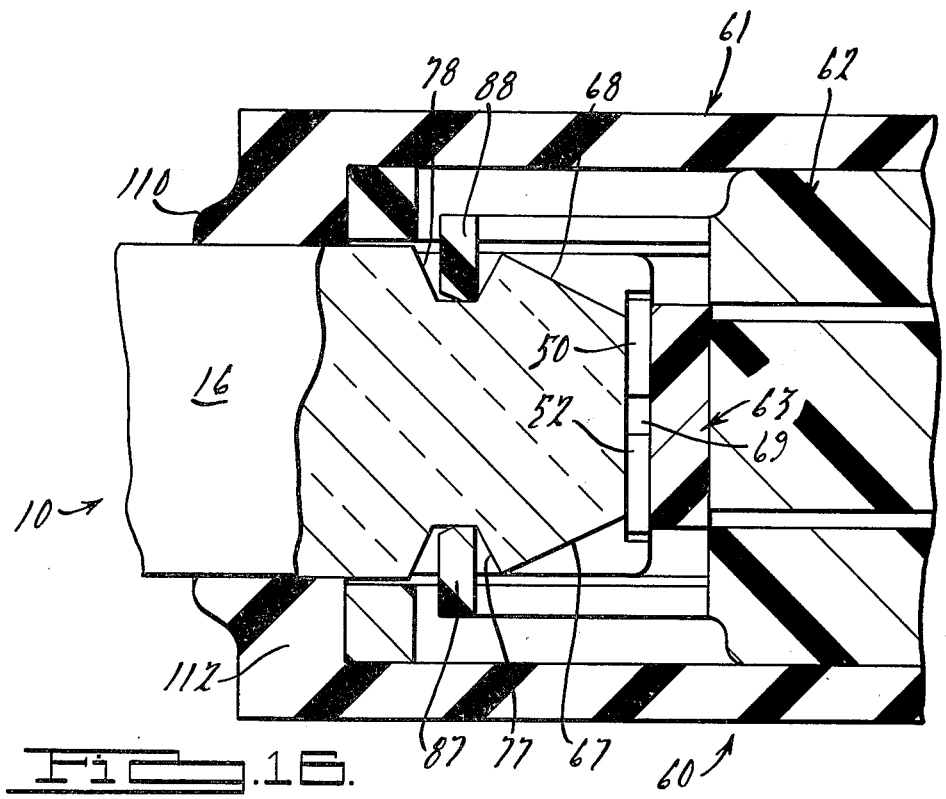

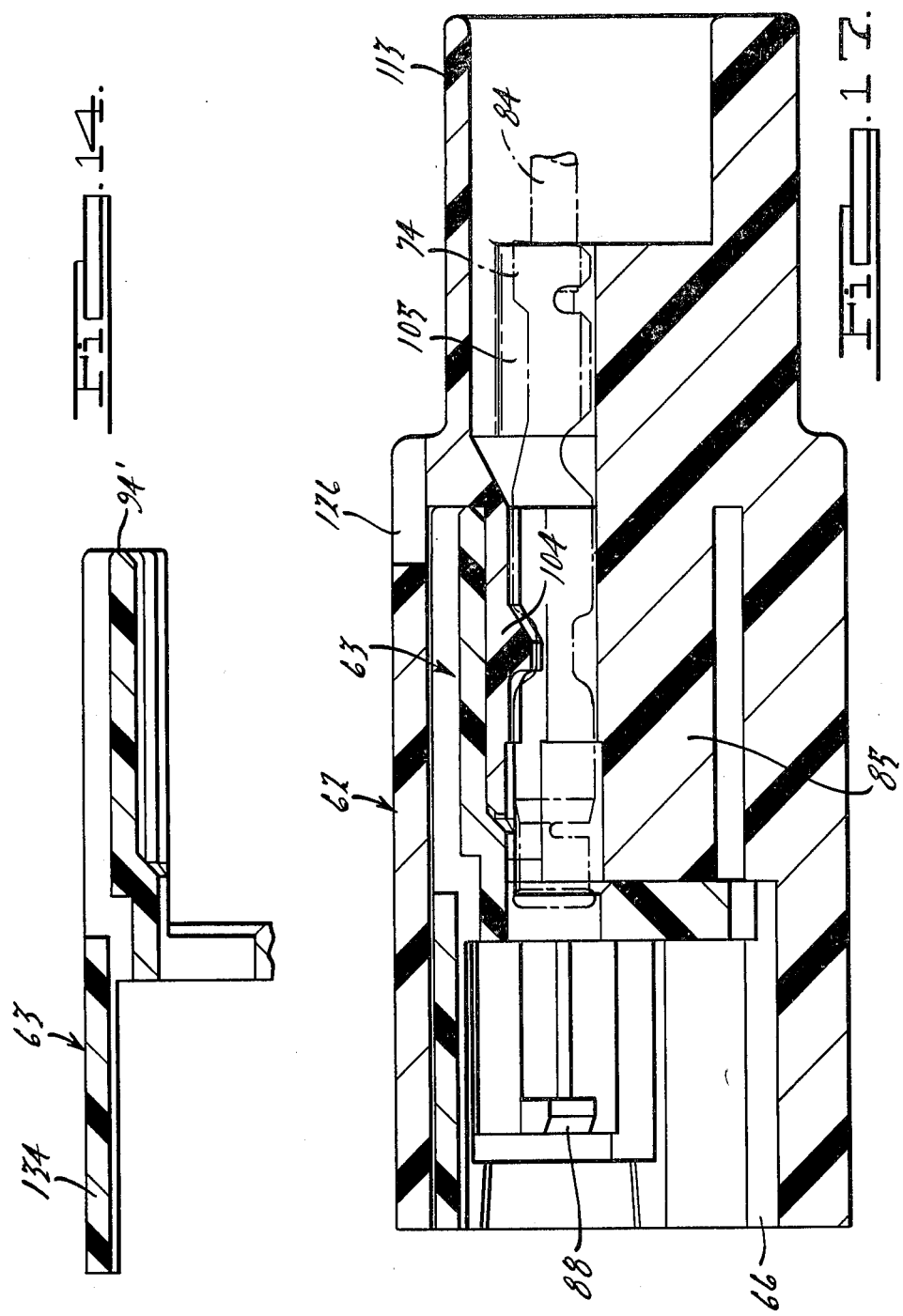

EXHAUST GAS OXYGEN SENSOR AND ELECTRICAL CONNECTOR ARRANGEMENT

BACKGROUND

This invention relates to an exhaust gas oxygen sensor and electrical connector arrangement for electrically connecting the oxygen sensor to an electronic device capable of utilizing an electrical signal produced by the oxygen sensor. The exhaust gas sensor is particularly suited for use in the measurement of the partial pressure of oxygen in the exhaust gases from an internal combustion engine and may be of the type having a ceramic, metal-oxide, oxygen-sensing element. Two metal oxide exhaust gas oxygen sensors are generally known, that is, titania oxygen sensors and zirconia oxygen sensors. Both of these exhaust gas oxygen sensor types are utilized in conjunction with electronic devices that, in response to an oxygen-sensor signal, provide electrical signals used in an engine control system to vary the air/fuel ratio of the mixture supplied to the engine for combustion.

The oxygen sensor and electrical connector arrangement of the invention was particularly designed for use with exhaust gas sensors of the titania type, but is equally adaptable to known oxygen sensors of the zirconia type. These sensors have a cylindrically-shaped member to which one or more electrical terminals are affixed for connection to an electronic circuit.

The oxygen sensors are designed for installation in the exhaust conduit of an internal combustion engine and are provided with threads designed to engage corresponding threads formed in an aperture in the exhaust conduit. Oxygen sensors of prior design have had a pigtail for electrical connection of the sensor to an electronic device. Cooperating male and female connectors have been required to interconnect the end of the pigtail with one or more electrical lead wires from the electronic device. At the connection of the pigtail to the oxygen sensor, a rubber boot has been provided to effect a leak-proof seal.

The exhaust gas sensor is located in an environment that is both very cold under certain environmental conditions and also very hot during normal sensor use. The exhaust gas sensor may reach temperatures up to about 850°C. or higher at the point at which it projects into the exhaust conduit. Moreover, the electrical connection at the oxygen sensor is subject to adverse road conditions that may include salt spray, humidity, water, oil, grease and the exhaust gases themselves. In the use of exhaust gas sensors in feedback fuel control systems, electrical connections between the sensor and the electronic device utilizing its signal are of great importance because failure of any of these connections or changes in their contact resistances can produce signal loss and failure of the closed-loop fuel control system for the engine.

SUMMARY OF THE INVENTION

In accordance with the invention, an exhaust gas oxygen sensor and electrical connector arrangement is provided for electrically connecting the oxygen sensor to an electronic device capable of utilizing an electrical signal produced by the oxygen sensor. The oxygen sensor and electrical connector arrangement in combination comprises an exhaust gas oxygen sensor and a connector assembly including a grommet, a sleeve and a spacer. Cooperating means, associated with the oxygen sensor and the connector assembly, provide a positive or latching connection therebetween. Also, connector terminal means, mounted within the connector sleeve, electrically connect a lead wire from the electronic device to one or more oxygen-sensor terminals.

The exhaust gas oxygen sensor has means to facilitate its mounting in the exhaust conduit of an engine. A ceramic metal-oxide oxygen-sensing element and at least one electrical conductor coupled to the oxygen-sensing element are provided. The oxygen sensor has a member of generally cylindrical shape. The electrical conductor from the metal-oxide oxygen-sensing element passes through the cylindrically-shaped member to an electrical terminal affixed to the member.

The connector assembly is used to provide electrical connection of a lead wire from the electronic device to the terminal on the cylindrically-shaped member of the oxygen sensor. For this purpose, the connector assembly includes an elastomeric grommet that cooperates with the cylindrically-shaped member of the sensor to provide a leak-proof contact or seal for the protection of the electrical connection. The sleeve of the connector assembly is received within the elastomeric grommet and retains the connector terminal means for interconnecting the electrical lead wire from the electronic device with the electrical terminal affixed to the cylindrically-shaped member of the oxygen sensor. The electrical interconnection is made when the grommet and sleeve are slipped or pushed over the cylindrically-shaped member of the oxygen sensor.

When the connector means is pushed over the cylindrically-shaped member of the sensor, a pawl on the sleeve of the connector assembly rides up a ramp formed in the surface of the cylindrically-shaped member and drops into a detent or the equivalent formed therein. This provides a positive latch connection between the connector assembly and the oxygen sensor. The cooperating means on the oxygen sensor and the connector assembly thus prevents separation of their mechanical and electrical connections.

The invention may be better understood by reference to the detailed description which follows and to the drawings.

BRIEF DESCRIPTION OF THE DRAWINGS

FIG. 1 is an elevational view of a combination exhaust gas oxygen sensor and electrical connector arrangement according to the invention;

FIG. 2 is an enlarged sectional view taken along the line II—II in FIG. 1 and shows the metal-oxide ceramic oxygen-sensing and thermistor elements of the titania oxygen sensor depicted in the combination of FIG. 1;

FIG. 3 is a sectional elevational view of enlarged scale, the section being taken along the line III—III in FIG. 2;

FIG. 4 is a sectional view taken along the line IV—IV in FIG. 3 and shows the terminal-pin end of the oxygen sensor ceramic insulator and its guide rib latching features;

FIG. 5 is a partial sectional view of the terminal-pin end (with the terminal pins removed) of the ceramic insulator shown in FIG. 4 and is taken along the line V—V in FIG. 4;

FIG. 6 is a sectional view of the oxygen sensor taken along the line VI—VI in FIG. 5 and illustrates the shape of the detents and guiding rib at this location on the oxygen sensor;

FIG. 7 is a view of the left end of the sleeve member of the connector assembly shown in FIG. 3;

FIG. 11 is a sectional view taken along the lines XI—XI in FIG. 7 and shows additional structural features of the sleeve of the connector assembly;

FIG. 12 is an end view of a spacer received within the sleeve of the connector assembly;

FIG. 13 is a sectional view of the spacer taken along the line XIII—XIII in FIG. 12;

FIG. 14, is a partial sectional view taken along the line XIV—XIV in FIG. 12;

FIG. 15 is a sectional view taken along the line XV—XV in FIG. 2 and shows the positive latching feature of the oxygen sensor and connector assembly;

FIG. 16 is a sectional view of the oxygen sensor and electrical connector arrangement taken along the line XVI—XVI in FIG. 15; and FIG. 17 is a sectional view of the assembled sleeve and spacer of the connector assembly showing in phantom a lead wire and connector terminal retained within the sleeve and maintained in this position by the spacer.

DETAILED DESCRIPTION

Figure 8:
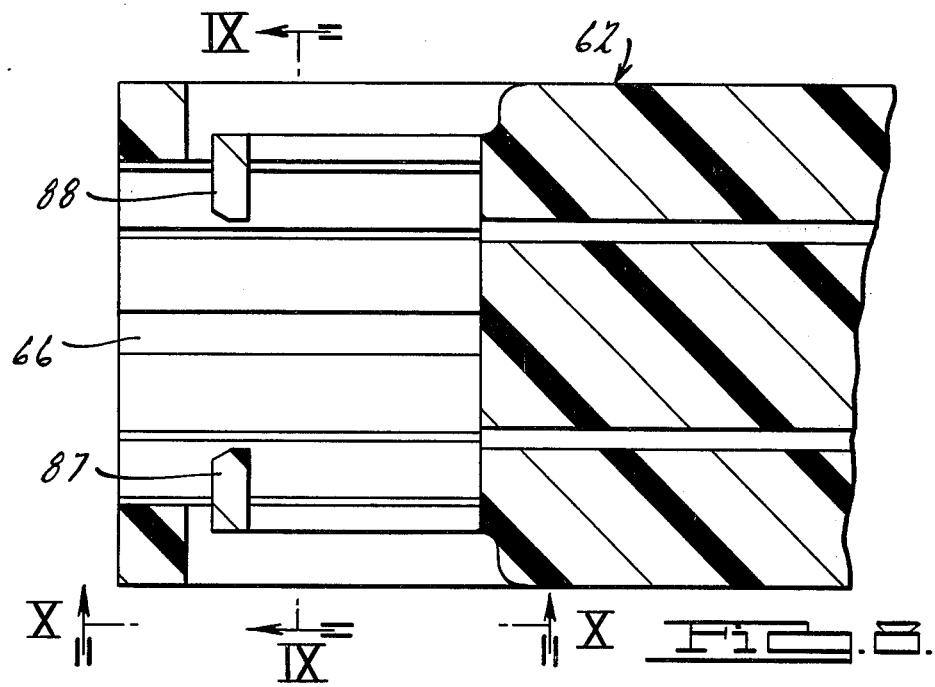
FIG. 8 is a sectional view taken along the line VIII—VIII in FIG. 7 and shows the pawls of the sleeve, which latch the sleeve to the detents of the cylindrically-shaped ceramic insulator of the oxygen sensor.
Figure 9:
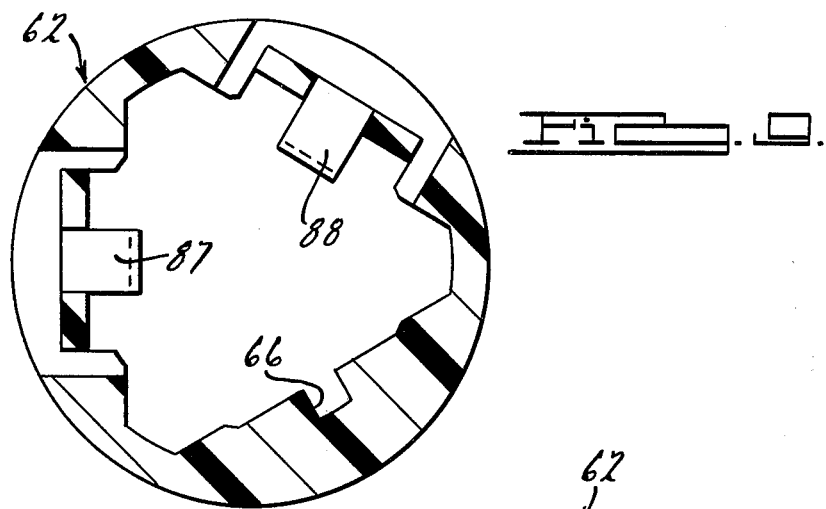
FIG. 9 is a sectional view taken along the line IX—IX in FIG. 8 and shows and pawls of the sleeve.
Figure 10:
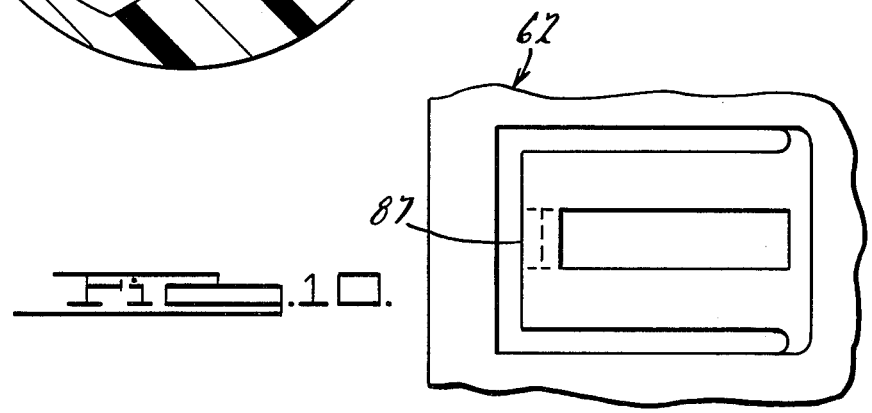
FIG. 10 is a view of a pawl of the sleeve and its pivotal connection with the remainder of the sleeve, as seen looking in the direction of the arrows X—X in FIG. 8.

With reference now to the drawings, wherein like numerals refer to like parts in the several views, there is shown in FIG. 1 in actual size, and in other Figures 2 to 17 in enlarged size, an exhaust gas oxygen sensor, generally designated by the numeral 10, together with a connector assembly, generally designated by the numeral 60. The exhaust gas oxygen sensor 10 and connector assembly 60 in combination form the exhaust gas oxygen sensor and electrical connector arrangement of the invention in its currently preferred form for use with an oxygen sensor 10 of the titania type hereinafter described. Sensors of the zirconia type also may be utilized with features of the electrical connector arrangement hereinafter described.

The exhaust gas sensor 10 has a body portion 12, which may be made of steel, and which has a threaded end 14 adapted to be received within a correspondingly threaded aperture in the exhaust conduit or manifold of an internal combustion engine. The sensor 10 also has a ceramic insulator 16 and a steel, perforated protection tube 18 surrounding the projecting end 26 of the ceramic insulator. The ceramic insulator also has a terminal-pin portion 28 hereinafter further described.

The projecting portion 26 of the exhaust gas sensor ceramic element 16 projects within the exhaust conduit of an internal combustion engine for the purpose of permitting exhaust gases therein to enter the protection tube 18 through its perforations and, thereby, to expose ceramic metal-oxide oxygen-sensing and thermistor elements 46 and 48 to exhaust gases. These elements 46 and 48 preferably are constructed as described in other commonly-assigned patents and patent applications. They are provided with electrodes connected to electrical conductors 30, 32 and 34 which pass through passages 20, 22 and 24, respectively.

These passages 20, 22 and 24 extend from the projecting portion 26 of the insulator 16 to its terminal-pin portion 28 at the opposite end. The portion 28 of insulator 16 is generally cylindrical in shape and has terminal pins 50, 52 and 54 mounted therein as may best be seen in FIG. 3. Oxygen sensors of the zirconia type have somewhat similar generally cylindrical members to which electrical terminals are affixed; these members are metal, the electrical terminals may be insulated from the metal member, and features of the present invention may be used.

The connector means 60 has brass connector terminal means in the form of devices 70, 72 and 74 which interconnect, respectively, the terminal pins 50, 52 and 54 with respectively corresponding electrical lead wires 80, 82 and 84. Each of the brass terminals 70 has two female ends, one of which receives one of the terminal pins of the exhaust gas oxygen sensor. The connector terminals within the connector assembly 60 are retained in position by retaining projections 100, 102 and 104.

The connector assembly 60, aside from the received oxygen sensor 10 and connector terminals 70, 72 and 74 and associated lead wires, comprises three main elements. The first of these is an elastomeric cover or grommet 61, which preferably is made from inherently-lubricated silicone elastomer. Within this elastomeric grommet 61, a sleeve 62 is received, this preferably being formed a high-performance grade of 30% glass-filled polybutylene terephthalate. The third main member of the connector assembly 60 is a spacer 63, which may be made from a material identical to that of the sleeve 62. If desired, the sleeve 62 and spacer 63 may be made of different colored materials, but must have melt characteristics suitable for its application; this is particularly important where high temperatures may be encountered.

It should be noted that contact between the sleeve and spacer members 62 and 63 of the connector assembly 60 with the exhaust gas sensor 10 is quite limited and is made between it and the ceramic insulator 16. In FIG. 3 it may be seen that the insulator 16 is received within a circular opening in the elastomeric grommet 61 which at its contact portion 110 forms a leak-proof seal with the cylindrical surface of insulator 16 to protect the electrical connections made within the interior of grommet 61. The seal is formed by the deformed lip portion 112 of the grommet 61, which lip portion extends radially inward with respect to the axis of the ceramic insulator 16. Also, the sleeve 62 of connector assembly 60 is retained within the elastomeric grommet 61 between its lip portion 112 and its rear portion 114. At the rear portion, wherein the electrical lead wires 80, 82 and 84 enter, a leak-proof seal also is maintained as may best be seen in FIG. 3. With respect to the elastomeric grommet 61, it may be seen in FIG. 1 that there is a flattened surface 64 that may be used for purposes of alignment of the terminal pins and connectors as the connector assembly is pushed over the cylindrically-shaped surface of the insulator 16 of the sensor.

With particular reference now to FIG. 4, there is shown an end view of the insulator 16 of the exhaust gas sensor 10. This view shows the end of the cylindrically-shaped insulator 16 in a position rotated 120° counter-clockwise with respect to what would be its proper orientation were the section to be reproduced as indicated by the cutting plane IV—IV in FIG. 3. Thus, the terminal pins 50 and 52 are oriented as shown and the terminal pin 54 also may be seen in cross-section behind pins 50 and 52. The conductors 30, 32 and 34 electrically connected to the sensing elements 46 and 48 are shown within the terminal pins. It may be seen that the conductors and the terminal-pin interiors are surrounded by a ceramic cement material, which maintains the position of the elecctrical conductors and retains the terminal pins within the ceramic insulator 16.

FIG. 5 is a section taken along the line V—V in FIG. 4 and shows the true length of the guide rib 65. For clarity of illustration, terminal pins 50 and 54 are not shown. It may be seen that the ramp 67 terminates in a detent 77. A similar ramp 68 terminates in a detent 78. The ramps, detents and the guide rib 65 are used to guide and latch the oxygen sensor and connector assembly together. The end face 69 of the insulator 16 limits the travel of the oxygen sensor into the connector assembly 60, the face 69 of the insulator abutting the left-hand end of the spacer 63 of the connector assembly, as may best be seen in FIG. 16.

FIG. 6 is a sectional view taken along the line VI—VI in FIG. 5 and further illustrates the shape of the detents 77 and 78.

With particular reference now to FIG. 7, there is shown a left-hand view of the sleeve 62 of the connector assembly 60. Both this component and the mating spacer 63 (FIGS. 12 to 14) may be injection molded. The sleeve 62 is generally cylindrical in shape, but has several slots and other openings in its exterior surface. It has a reduced diameter at its right-hand end 113 (FIG. 11) and has three ribs in this portion. These ribs in FIGS. 7 and 11 are identified by the numerals 105, 106 and 107. These and other features of the sleeve should be viewed in connection with FIGS. 8, 9, 10 and 11. In FIG. 11, the ribs 105 and 106 may be seen coming together in the center portion of the right-hand end 113 of the sleeve 62. The rib 106 has a portion at its right-hand side which may be used to fix its location within the elastomeric grommet 61.

The left-hand end of the sleeve 62 has a central portion 85 that projects axially upward as viewed in FIG. 7 and has three radii formed in it suitable for receipt of the connector terminals 70, 72 and 74. The three connecting terminals are received in the spaces thus formed and are secured by the retaining projections 100, 102 and 104. The retaining projections engage a reduced-diameter portion of each connector terminal. To maintain the connector terminals within the sleeve in an immobile position, the spacer 63 is made to slide into mating engagement with the sleeve 62. As a result, the spacer latches 120 and 122 become latched in the locations 126, as may best be seen in FIG. 3. The spacer 63 separates the retaining projections 100 and 102 from the respectively contacted outer parts 110 and 112 of the sleeve 62, thereby, to prevent resilient pivoting of the retaining projections away from the reduced-diameter portions of the connecting terminals. The spacer member serves to latch itself in position such that the assembly of the sleeve and spacer becomes relatively permanent. Axial movement is prevented of the connecting terminal pins of the exhaust gas sensor. The sleeve 62 is restrained with respect to axial movement within the elastomeric grommet 61.

With reference once again to FIGS. 7 through 11, it may be moted that the retaining projections 100, 102 and 104 are pendantly mounted and in alignment with the centers of the radii defining the central portion 85 of the sleeve 62. In addition to these pendantly mounted devices, pawls 87 and 88 are provided for travelling, respectively, up the ramps 67 and 68 and, upon passing the ramps, the pawls are resiliently urged into the corresponding detents 77 and 78 of the insulator 16. In this travel, the slot 66 in the sleeve (FIG. 7) receives the guide rib 65 of the insulator 16 as the sleeve slides over the insulator prior to being latched thereto. The shape of the pawls, and their pivotal and resilient fabrication as a part of the sleeve, may best be seen in FIGS. 8, 9 and 10. The manner in which the pawls 87 and 88 latch with the insulator may be seen in sectional view in FIGS. 15 and 16. In particular, in FIG. 16, it may be seen that the pawls 87 and 88 have travelled up the ramps 67 and 68 and have been received in the detents 77 and 78 to retain the connector assembly 60 on the exhaust gas sensor 10.

With particular reference now to FIGS. 12, 13, 14, and 17, there may be seen the spacer 63 and its assembly with the sleeve 62. In FIG. 12, it may be seen that the spacer 63 has three equally-spaced openings 140, 142 and 144 which receive the connnector terminals 70, 72 and 74 and the corresponding exhaust gas sensor terminal pins 50, 52 and 54 at their point of joinder. The spacer has extending members 90', 92' and 94' which have channels that cooperatively receive, in sliding relationship, complementary-shaped portions 90, 92 and 94 of the pendantly mounted retaining projections 100, 102 and 104. The elongated portions 130, 132 and 134 of the spacer 63 are positioned within the connector assembly as indicated in FIG. 3.

In FIG. 7, the shape or contours of the surfaces 90, 92 and 94 of the retaining projections 100, 102 and 104 may be seen; these surfaces cooperatively mate and slide in the channels 90', 92' and 94' of the spacer shown in FIG. 13. FIG. 14 illustrates the shape of the extending portion 94' of the spacer, which cooperates with the retaining projection 104 of the sleeve 62.

Based upon the foregoing description of the invention, it may be seen that a combination of devices has been described wherein an exhaust gas sensor cylindrically-shaped member having one or more terminal pins affixed to it is electrically and mechanically connected with one or more corresponding lead wires and connector terminals. This facilitates connection to an electronic device that would utilize the signal produced by the exhaust gas sensor. The mechanical connection to the exhaust gas sensor is leak-proof and is designed to withstand the temperature and environment encountered at the location of an oxygen sensor in the exhaust conduit of an internal combustion engine of a motor vehicle.

What is claimed is:

1. An exhaust gas oxygen sensor and electrical connector arrangement for electrically connecting the oxygen sensor to an electronic device capable of utilizing an electrical signal produced by the oxygen sensor, the oxygen sensor and electrical connector in combination comprising:

(a) an exhaust gas sensor having means to facilitate its mounting in the exhaust conduit of an engine, a ceramic metal-oxide oxygen-sensing element, at least one electrical conductor coupled to the oxygen-sensing element, a member of generally cylindrical shape through which the electrical conductor passes, and an oxygen sensor electrical terminal affixed to the cylindrically-shaped member and electrically connected to the conductor coupled to the oxygen-sensing element;

(b) at least one lead wire for use in coupling the oxygen-sensor terminal to the electronic device;

(c) a connector assembly for providing electrical connection of the lead wire to the oxygen-sensor terminal affixed to the cylindrically-shaped member and to provide a leak-proof contact with the cylindrically-shaped member for the protection of the electrical connection, the connector assembly comprising a grommet and a sleeve received within the grommet, the grommet being formed from elastomeric material and the cylindrically-shaped member of the oxygen sensor being partially received within the grommet, the grommet forming a leak-proof contact with the surface of the cylindrically-shaped member;

(d) cooperating means, associated with the oxygen sensor cylindrically-shaped member with the sleeve of the connector assembly, for forming a latching connection therebetween; and (e) connector terminal means, mounted within the sleeve of the connector assembly, for electrically connecting the lead wire to the oxygen-sensor terminal when the sleeve of the connector assembly and the cylindrically-shaped member of the oxygen sensor are latched together with their cooperating means.

2. An oxygen sensor and electrical connector arrangement according to claim 1, wherein the cooperating means comprises a ramp and detent on the cylindrically-shaped member and a pawl on the sleeve of the connector assembly, the pawl cooperating with the ramp and detent to form the latching connection when the sleeve of the connector assembly is pushed over the cylindrically-shaped member.

3. An oxygen sensor and electrical connector arrangement according to claim 2, wherein the pawl is formed from the material of the sleeve and is resiliently pivoted at its connection to the sleeve, the pawl moving along the ramp on the cylindrically-shaped member when the sleeve is pushed over it, the pawl being resiliently urged into the detent after passing the end of the ramp.

4. An oxygen sensor and electrical connector arrangement according to claim 1, wherein the grommet has a lip portion extending radially inwardly with respect to the axis of the cylindrically shaped portion, the leak-proof contact of the grommet with the cylindrically-shaped member being formed at the lip portion of the grommet, the lip portion being deformed at its location of contact with the cylindrically-shaped member.

5. An oxygen sensor and electrical connector arrangement according to claim 1, wherein the connector assembly includes a spacer having a portion thereof in contact with the end of the cylindrically-shaped member of the oxygen sensor.

6. An oxygen sensor and electrical connector arrangement according to claim 5, wherein the spacer has a second portion received between two parts of the sleeve, one of those parts limiting movement of the connector terminal means as a result of the position of the spacer second portion, and the other sleeve part, limiting movement of the spacer relative to the sleeve once the spacer is positioned to limit movement of the connector terminal means.

7. An oxygen sensor and electrical connector arrangement according to claim 5, wherein the sleeve has a retaining projection engaging the connector terminal means mounted within the sleeve to limit movement of the connector terminal means, the spacer preventing disengagement of the retaining projection.

8. An oxygen sensor and electrical connector arrangement according to claims 5, 6 or 7 wherein the spacer second portion mates with the one part of the sleeve, sliding movement between the spacer second portion and the one part of the sleeve resulting in latching of the spacer to the sleeve and latching of the sleeve to the spacer.

* * * * *